United States Patent
Okano et al.

(10) Patent No.: US 9,981,064 B2
(45) Date of Patent: May 29, 2018

(54) REGENERATED CORNEAL ENDOTHELIAL CELL SHEETS, PROCESSES FOR PRODUCING THE SAME, AND METHODS OF USING THE SAME

(75) Inventors: Teruo Okano, Ichikawa (JP); Kohji Nishida, Ibaraki (JP); Masayuki Yamato, Setagaya-ku (JP)

(73) Assignees: CELLSEED INC., Tokyo (JP); Kohji Nishida, Osaka (JP)

( * ) Notice: Subject to any disclaimer, the term of this patent is extended or adjusted under 35 U.S.C. 154(b) by 587 days.

(21) Appl. No.: 10/546,275

(22) PCT Filed: Feb. 20, 2004

(86) PCT No.: PCT/JP2004/001975
§ 371 (c)(1),
(2), (4) Date: Jun. 15, 2006

(87) PCT Pub. No.: WO2004/073761
PCT Pub. Date: Sep. 2, 2004

(65) Prior Publication Data
US 2007/0148137 A1    Jun. 28, 2007

(30) Foreign Application Priority Data
Feb. 20, 2003 (JP) ................................ 2003-089300

(51) Int. Cl.
| C12N 5/00 | (2006.01) |
| A61L 27/38 | (2006.01) |
| A61L 27/50 | (2006.01) |
| C12N 5/079 | (2010.01) |

(52) U.S. Cl.
CPC ....... *A61L 27/3808* (2013.01); *A61L 27/3839* (2013.01); *A61L 27/3895* (2013.01); *A61L 27/50* (2013.01); *C12N 5/0621* (2013.01); *A61L 2430/16* (2013.01); *C12N 2539/10* (2013.01)

(58) Field of Classification Search
CPC ............. A61L 27/3808; A61L 27/3895; C12N 5/0621
See application file for complete search history.

(56) References Cited

U.S. PATENT DOCUMENTS

| 4,842,599 A * | 6/1989 | Bronstein ............... A61F 2/142 623/5.15 |
| 2003/0036196 A1 | 2/2003 | Okano et al. |
| 2004/0009566 A1 | 1/2004 | Okano et al. |
| 2004/0028657 A1 | 2/2004 | Okano et al. |
| 2006/0234377 A1 | 10/2006 | Okano et al. |
| 2006/0240400 A1 | 10/2006 | Yamato et al. |
| 2006/0240552 A1 | 10/2006 | Yamato et al. |
| 2007/0092492 A1 | 4/2007 | Matsuda et al. |
| 2007/0148137 A1 | 6/2007 | Okano et al. |
| 2008/0118474 A1 | 5/2008 | Okano et al. |
| 2008/0131476 A1 | 6/2008 | Kanzaki et al. |
| 2008/0226692 A1 | 9/2008 | Sato et al. |
| 2008/0289052 A1 | 11/2008 | Okano et al. |
| 2011/0229962 A1 | 9/2011 | Mizutani et al. |
| 2012/0107930 A1 | 5/2012 | Sasaki et al. |
| 2012/0156781 A1 | 6/2012 | Takahashi et al. |
| 2012/0210451 A1 | 8/2012 | Shimizu et al. |

FOREIGN PATENT DOCUMENTS

| EP | 1312669 A1 | 5/2003 |
| EP | 1598417 A1 | 11/2005 |
| EP | 1602383 | 12/2005 |
| JP | 2003-38170 | 2/2003 |
| WO | 98/31316 | 7/1908 |
| WO | 01/68799 A1 | 9/2001 |
| WO | 02/10349 A1 | 2/2002 |
| WO | 2004/069295 A1 | 8/2004 |
| WO | 2004/070023 A1 | 8/2004 |
| WO | 2004/073761 A1 | 9/2004 |

OTHER PUBLICATIONS

Int'l Preliminary Report on Patentability for PCT/JP2004/001975, dated Feb. 2006, six pages.
Kikuchi et al. "Two-dimensional amnipulation of confluently cultured vascular endothelial cells using tmperature-responsive poly(N-isopropylacrylamide)-grafted surfaces" J. Biom. Sci. Polymer Edn. 9:1331-1348 (1998).
Int'l Search Report for Int'l Application No. PCT/JP2004/001975, completed Apr. 2004.
International Search Report for PCT/JP2004/001975 dated May 11, 2004.
Nishida "Kakumaku Johi, Kakumaku Naihi no Saisei Iryo" Biomaterials—Seitai Zairyo 20:259-268 (2002).
Yamato et al. "Saibo Sheet Kogaku no Sosei" Biomaterials—Seitai Zairyo 21:46-52 (Jan. 2003).
Supplementary European search report for related Application No. 04713172.7, four pages, dated Jan. 28, 2011.
Kinoshita "Ocular surface reconstruction by tissue engineering" Nippon Ganka Gakkai Zasshi 106:837-868 (Accession No. NLM12610839, English abstract only) (Dec. 2002).

* cited by examiner

Primary Examiner — Marcia S Noble
(74) Attorney, Agent, or Firm — Nixon & Vanderhye PC

(57) ABSTRACT

An improved process for producing a regenerated corneal endothelial cell sheet, comprising the steps of allowing corneal endothelial cells collected from a tissue to be cultivated on a cell culture support having its surface covered with a polymer of which the hydrating force varies in a temperature range of 0-80° C., and after the culture,
(1) adjusting the temperature of the culture solution to the temperature at which the polymer on the substrate surface is hydrated,
(2) bringing the cultured corneal endothelial cell sheet into close contact with a carrier, and
(3) detaching the sheet together with the carrier.
The regenerated corneal endothelial cell sheet obtained by the process will adhere very well to living tissues.

20 Claims, 6 Drawing Sheets

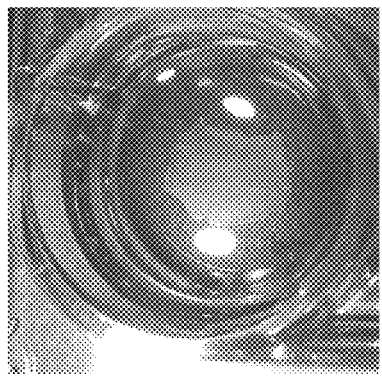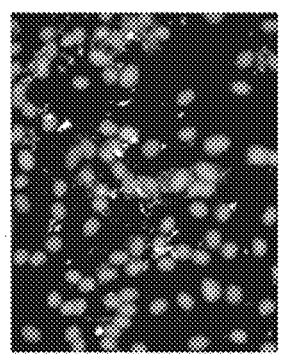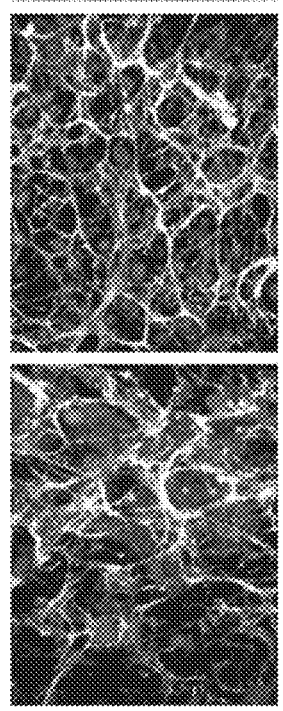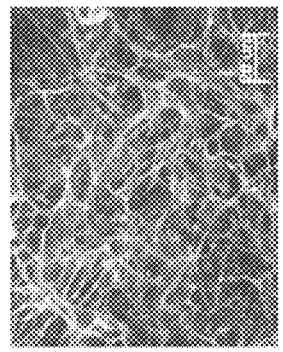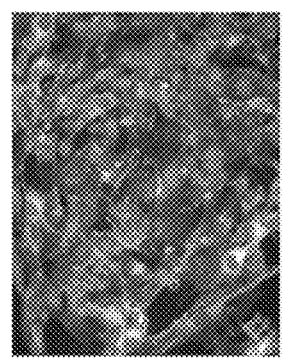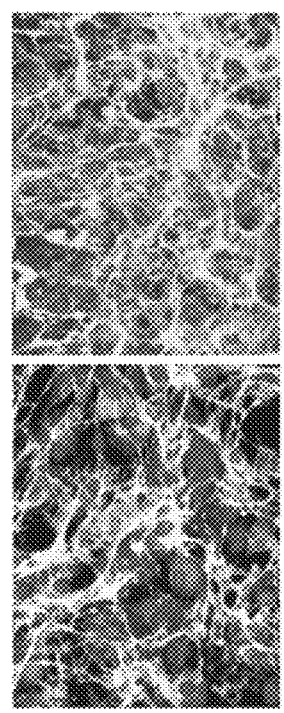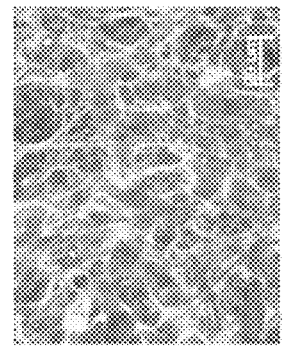

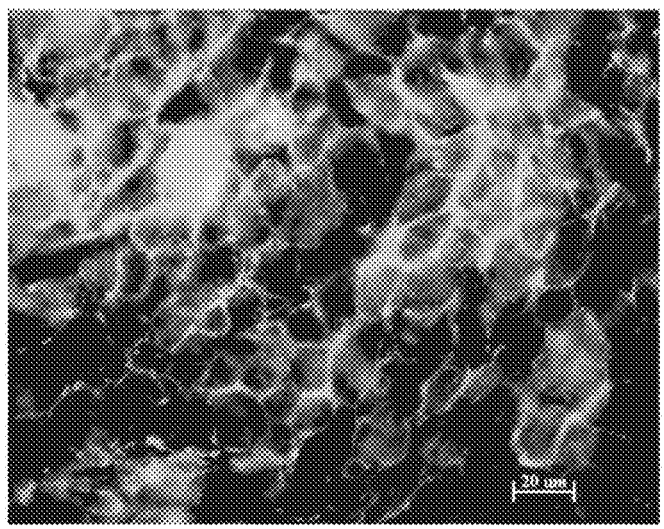
FIG. 3
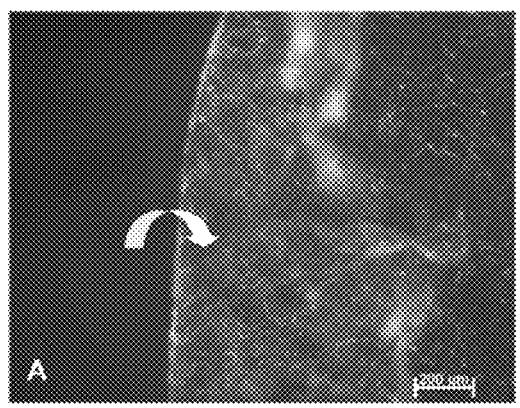 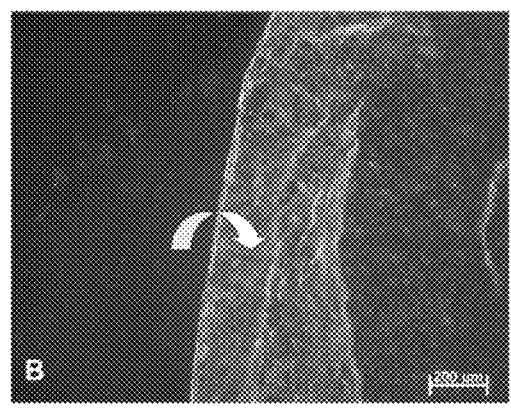
FIG. 4A  FIG. 4B

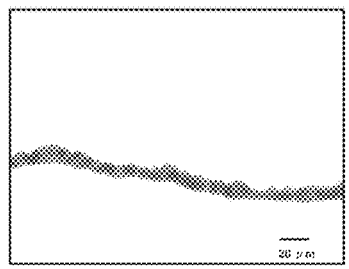 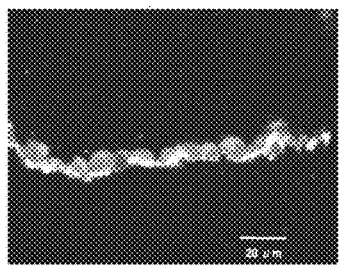 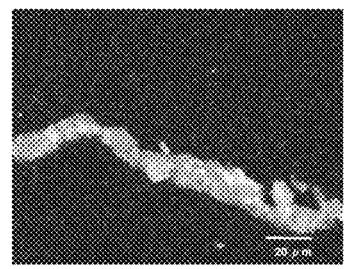
FIG. 5A          FIG. 5B          FIG. 5C
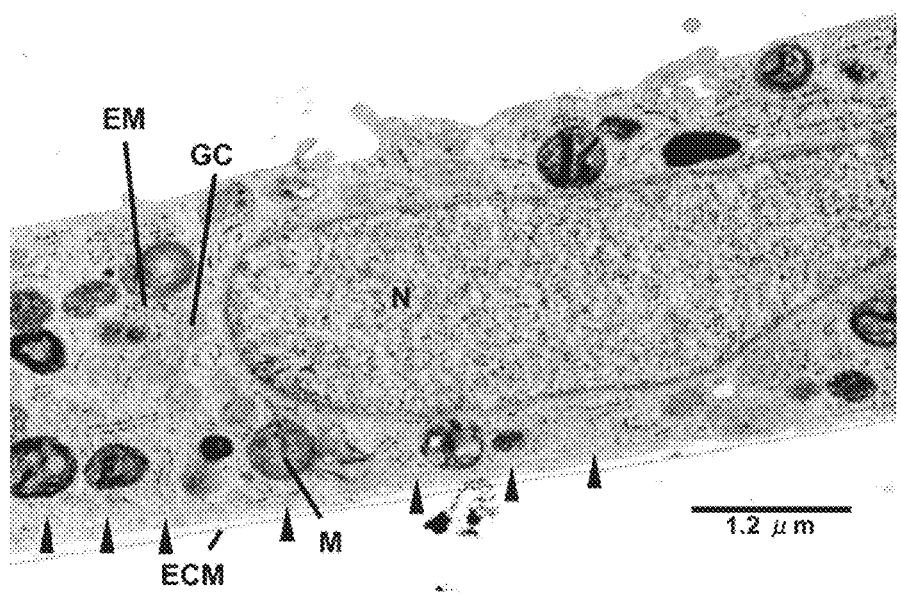
FIG. 6

S  D  T

REGENERATED CORNEAL ENDOTHELIAL CELL SHEETS, PROCESSES FOR PRODUCING THE SAME, AND METHODS OF USING THE SAME

This application is the US national phase of international application PCT/JP2004/001975, filed 20 Feb. 2004, which designated the U.S. and claims benefit of JP 89300/2003, filed 20 Feb. 2003, the entire contents of each of which are hereby incorporated by reference.

TECHNICAL FIELD

This invention relates to regenerated corneal endothelial cell sheets in biology, medicine and other fields, as well as processes for producing such sheets, and therapeutic methods using them.

BACKGROUND ART

The corneal tissue consists of five layers, a corneal epithelium layer on the outermost surface, Bowman's membrane, a corneal stromal layer, Descemet's membrane, and a corneal endothelium layer. The innermost corneal endothelium layer serves as a liner on the corneal tissue, and Descemet's membrane corresponds to the basement membrane of the corneal endothelial layer which is composed of adhesive proteins. The function of corneal endothelial cells is to pump water out of the corneal stroma into the anterior chamber counteracting the swelling pressure of the stroma, presumably due to the pumping action as assisted by Na—K ATPase. Human corneal endothelial cells will not usually undergo cell division in the living body, and denatured or exfoliated endothelial cells are compensated for by the thickening or migration of the remaining cells. If the remaining corneal endothelial cells are too few, the pumping function of the corneal endothelial tissue is no longer adequate and the corneal tissue swells to develop diseases such as corneal endothelial disorder and bullous keratopathy. Therapies of these diseases include the use of therapeutic soft contact lenses to deal with eye pain and the use of ophthalmic ointments and eye drops of hypertonic saline in order to remove water from the swollen corneal tissue; however, these methods are just symptomatic and radical therapies that affect the basic underlying causes of the symptoms have been desired.

With marked advances in medical technology, it has recently become popular to perform organ transplants, i.e., replacing a difficult-to-treat organ with another person's organ. This is also true with diseases such as the above-mentioned corneal endothelial disorder and bullous keratopathy and attempts are being made to treat them radically by transplanting all layers of the cornea. However, the number of donors in Japan is still considerably smaller than that of patients and while there are annually about 20,000 patients who need keratoplasty, only a tenth of them (ca. 2,000 in number) can actually be treated by that procedure. Although keratoplasty is a virtually established procedure, it suffers the problem of shortage in donors, giving rise to the need for the development of a next-generation medical procedure.

As a means of solving this problem, the technology of regenerative medicine which involves obtaining a required tissue by artificial in vitro cultivation has recently seen a rapid advance. Conventionally, such cell culture has been performed either on the surface of glass or on the surface of synthetic polymers that were subjected to a variety of treatments. For example, a variety of polystyrene vessels that were subjected to surface treatments such as γ-ray irradiation and silicone coating have become popular for use in cell culture. However, the above-mentioned corneal endothelial cells are known to be cells that are difficult to grow in high density on the surfaces of such vessels and a better method of culture has been desired.

Cells that have been cultivated to grow on vessels for cell culture are detached and recovered from the surfaces of the vessels by treatment with proteolytic enzymes such as trypsin or chemical reagents. However, it has been pointed out that the recovery of grown cells by treatment with chemical reagents involves some disadvantages such as an increased chance of contamination by impurities and the grown cells becoming denatured or damaged by the chemical treatment to have their inherent functions impaired. In order to overcome these disadvantages, several techniques have been proposed to date.

JP 2-23191 B describes a method for producing a transplantable membrane of keratin tissue which comprises the steps of cultivating human neonatal keratinized epidermic cells in a culture vessel under conditions that enable a membrane of keratin tissue to form on the surface of the vessel and detaching the membrane of keratin tissue using an enzyme. Specifically, with 3T3 cells used as a feeder layer, the epidermic cells are grown and stratified as a cell sheet which is recovered using the proteolytic enzyme dispase. However, the method described in JP 2-23191 B has had the following defects.

(1) Dispase is of microbial origin and the recovered cell sheet needs to be washed thoroughly.
(2) The conditions for dispase treatment differ from one batch of cell culture to another and great skill is required in the treatment.
(3) The cultured epidermic cells are pathologically activated by dispase treatment.
(4) The extracellular matrix is decomposed by dispase treatment.
(5) As the result, the diseased part to which the cell sheet has been grafted is prone to infection.

In addition to these defects of the prior art method, corneal endothelial cells that are contemplated in the present invention do not have as strong intercellular binding as dermal cells and have had the problem that cultivated cells cannot be detached and recovered as a single sheet even if the dispase is employed.

In Japanese Patent Application No. 2001-226141, anterior segment related cells are cultivated on a cell culture support comprising a substrate having its surface coated with a temperature responsive polymer having an upper or lower critical temperature of 0-80° C. at which it dissolves in water and, if necessary, the cultured cell layer is stratified by the usual method and the cultured cell sheet is detached by merely changing the temperature of the support. The detached cell sheet has adequate strength. However, considering the take and functions of the corneal endothelial cell sheet that is actually obtained, further improvements have been desired.

DISCLOSURE OF THE INVENTION

The present invention has been accomplished with a view to solving the aforementioned problems of the prior art. Therefore, the present invention has as an object providing a regenerated corneal endothelial cell sheet that adheres well to ocular tissues. Other objects of the present invention are to provide a process for producing the cell sheet and a method of using it.

In order to attain the stated objects, the present inventors engaged in R&D activities taking various angles of study. As a result, the inventors found that a regenerated corneal endothelial cell sheet that would adhere very well to a living tissue could be obtained by a process comprising the steps of cultivating corneal endothelial cells under specified conditions on a cell culture support comprising a substrate having its surface covered with a specified temperature responsive polymer, thereafter adjusting the temperature of the culture solution to the temperature at which the polymer on the substrate surface hydrates, bringing the cultured, regenerated corneal endothelial cell sheet into close contact with a specified carrier, and detaching the sheet together with the carrier while care is taken to inhibit the shrinkage of the sheet. The present invention has been accomplished on the basis of this finding.

Thus, the present invention first provides a regenerated corneal endothelial cell sheet in close contact with a carrier that will adhere well to an anterior segment tissue and which comprises a functionally sufficient cell density.

The present invention also provides a process for producing a regenerated corneal endothelial cell sheet, comprising the steps of cultivating cells on a cell culture support comprising a substrate having its surface covered with a temperature responsive polymer that dehydrates in a temperature range of 0-80° C., and thereafter, (1) adjusting the temperature of the culture solution to the temperature at which the polymer on the substrate surface is hydrated, (2) bringing the cultured corneal endothelial cell sheet into close contact with a carrier, and (3) detaching the sheet together with the carrier.

In addition, the present invention provides a method of treatment comprising grafting the above-mentioned, regenerated corneal endothelial cell sheet.

Further in addition, the present invention provides the above-mentioned, regenerated corneal endothelial cell sheet for the treatment of a wounded tissue.

BRIEF DESCRIPTION OF THE DRAWINGS

FIG. 1 shows a regenerated corneal cell sheet as detached from the cell culture support material in Example 4.

FIGS. 2A-2H show the results of cultivating the human regenerated corneal cell sheet in Example 4, recovering it at day 1 (FIGS. 2A and 2E), day 3 (FIGS. 2B and 2F), day 7 (FIG. 2C and 2G) and day 14 (FIGS. 2D and 2H), and staining the produced collagen IV (FIGS. 2A-2D) and fibronectin (FIGS. 2E-2H) in accordance with the usual method.

FIG. 3 shows the result of immunofluorescent staining of ZO-1 protein in the regenerated corneal endothelial cell sheet at day 4 of culture in Example 4.

FIGS. 4A-4B show the results of staining, in accordance with the usual method, of the collagen IV (FIG. 4A) and fibronectin (FIG. 4B) present in the human regenerated corneal cell sheet as it was being detached in Example 4; the arrows indicate the direction of detachment.

FIGS. 5A-5C show the results of H/E staining of the human regenerated corneal cell sheet as it was detached in Example 4 (FIG. 5A), as well as the results of staining, in accordance with the usual method, of the collagen IV (FIG. 5B) and fibronectin (FIG. 5C) present in the detached cell sheet.

FIG. 6 shows a TEM image of the human regenerated corneal cell sheet obtained in Example 4: ECM, extracellular matrix; N, nucleus; GC, Golgi complex; M, mitochondrion; EM, endoplasmic reticulum; the arrows indicating intracellular binding.

FIG. 7A shows the result of measuring the protein on the surface layer of the cell sheet by staining with Coomassie Brilliant Blue, and FIG. 7B shows the result of staining with an anti-human ZO-1 polyclonal antibody; T, the result of the cell sheet as detached by low-temperature treatment from the cell culture support material of the present invention; D, the cells obtained by dispase treatment from a commercial substrate uncovered with a temperature responsive polymer; S, the result of analysis of cells as detached from that commercial substrate by a scraper method.

FIG. 8A shows the result of observing the cultured cell sheet from above, and FIG. 8B shows the result of observation in the thickness direction.

BEST MODES FOR CARRYING OUT THE INVENTION

Figure 7A:
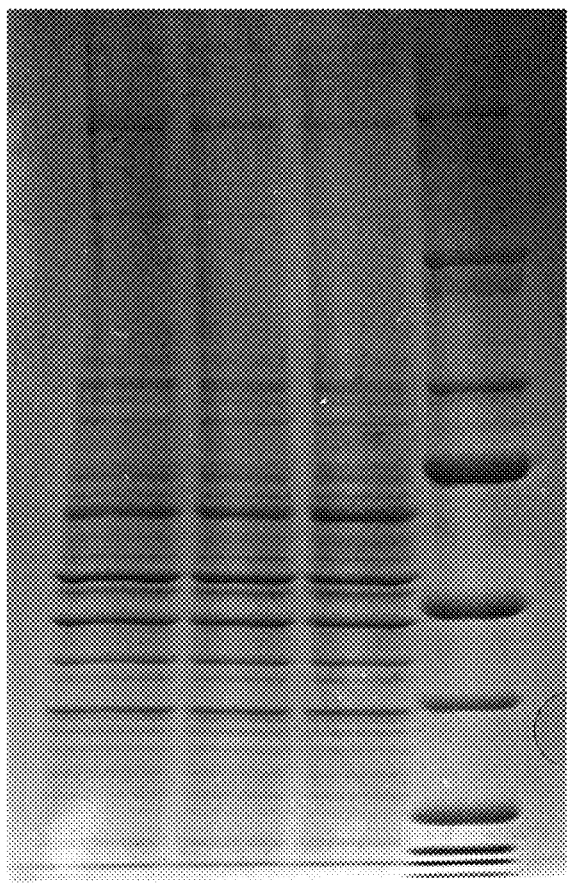
FIGS. 7A-7B show the results of an experiment in which the protein on the surface layer of each of the corneal endothelial cell sheets shown in Example 5 and Comparative Examples 3 and 4 and the ZO-1 protein participating in intracellular binding were verified by SDS-PAGE.

A typical endothelial cell to be used in the present invention is corneal endothelial cells in the corneal tissue but the applicable cells are by no means limited in type. In the present invention, the regenerated corneal endothelial cell sheet means a sheet that is obtained by cultivating a single layer of the above-described various cells on a culture support and thereafter detaching the layer from the support.

The regenerated corneal endothelial cell sheet in the present invention is such that it has not been damaged during cultivation by proteolytic enzymes typified by dispase and trypsin. Therefore, the regenerated corneal endothelial cell sheet as detached from the substrate retains the intercellular desmosome structure, has only a few structural defects, and features high strength. In addition, the sheet of the present invention is characterized in that the basement membrane-like protein formed between cell and substrate during cultivation has not been destroyed by enzyme. Hence, the sheet can attach satisfactorily to the tissue of the diseased part to which it has been grafted and this enables an efficient treatment to be performed. This is described below more specifically. If an ordinary proteolytic enzyme such as trypsin is employed, the intercellular desmosome structure and the basement membrane-like protein between cell and substrate are hardly retained and, hence, the cell sheet is detached with the cells separated into discrete masses. As for the proteolytic enzyme dispase, the cell sheet can be detached with 10-60% of the intercellular desmosome structure being retained; however, almost all of the basement membrane-like protein between cell and substrate is destroyed and the cell sheet obtained has only low strength. In contrast, the cell sheet of the present invention keeps at least 80% of each of the desmosome structure and the basement membrane-like protein intact, thus providing the various advantages described above.

The regenerated corneal endothelial cell sheet in the present invention shows a very good take on the anterior segment tissue which is a living tissue. The present inventors have found that this property was realized by inhibiting the shrinkage of the regenerated corneal endothelial cell sheet as detached from the support's surface. Desirably, the shrinkage of the corneal endothelial cell sheet is no more than 20% in length in any of the directions in the sheet, preferably 10% or less, and more preferably 5% or less. If the shrinkage is more than 20% in length in any of the directions of the sheet, the detached cell sheet will be in a slack state; in such a state, the sheet cannot be brought into close contact with the living tissue and the "high take" intended by the present invention is not attainable.

The method of preventing the shrinkage of the regenerated corneal endothelial cell sheet is not limited in any particular way as long as it will not cause the cell sheet to shrink; in one example, an annular carrier with a cutout in the center is placed in close contact with the regenerated corneal endothelial cell sheet, which is then detached from the support together with the carrier.

The carrier which is to be placed in close contact with the regenerated corneal endothelial cell sheet is a structure that keeps the cell sheet of the present invention from shrinking and may be realized by a polymer membrane or a structure molded from a polymer membrane, or a metallic fixture. If a polymer is to be used as the carrier material, specific examples include polyvinylidene difluoride (PVDF), polypropylene, polyethylene, celluloses, cellulose derivatives, papers, chitin, chitosan, collagen, urethane, etc.

The term "close contact" as used herein refers to such a state that the cell sheet does not shrink by slipping or moving on the carrier along the interface between the cell sheet and the carrier; the two members may be placed in close contact by being bound physically or with an intervening liquid (e.g. the culture solution or other isotonic fluid) in between.

The shape of the carrier is not limited in any particular way but if the regenerated corneal endothelial cell sheet obtained is grafted together with a carrier that has a cutout in a selected area which is about the same size as or larger than the site of grafting, great convenience is offered since the cell sheet is fixed only to the periphery of the cutout and just needs to be pressed through it to contact the site of grafting. Since the corneal endothelial tissue is located in the innermost layer of the corneal tissue, another possible grafting method is such that the side of the cell sheet which is opposite the side in contact with its support is secured to a fixture, which is inserted as such into the corneal tissue and left behind in it. The shape of the fixture used for this purpose is not limited in any particular way but two examples that are easy to handle and convenient are a fixture having a curved surface with the same curvature as the morphology of the corneal endothelial tissue in the living body and a fixture which is identical to the first mentioned fixture except that it has a suction port that assists with securing of the cell sheet.

The high take the regenerated corneal endothelial cell sheet of the present invention characteristically exhibits on the living tissue is realized under specified culture conditions Briefly, the cell sheet of the present invention is obtained by inoculating corneal endothelial cells on a substrate's surface and it has been found that the sheet is preferably detached not earlier than 10 days, more preferably not earlier than 12 days, most preferably not earlier than 20 days, after the cells have reached confluence on the substrate's surface. If the period of cultivation is shorter than 10 days, the regenerated corneal endothelial cell sheet as detached does not have an adequate basement membrane and the sheet's adherence decreases accordingly, with the result that the "high take" which characterizes the present invention is not attainable.

The regenerated corneal endothelial cell sheet of the present invention is a highly populated cell sheet having the inherent function of the corneal endothelial tissue. It has been found that the sheet has a cell density of at least 2,500 cells/mm$^2$, preferably at least 2,700 cells/mm$^2$, and more preferably at least 2,900 cells/mm$^2$. Below 2,500 cells/mm$^2$, the cell sheet cannot develop adequate pumping function, thus failing to exhibit high functionality which is one of the characteristic features of the present invention.

The regenerated corneal endothelial cell sheet in the present invention is a cell sheet having adequate pumping function. It has been found that the number of pump sites (Na/K ATPase pump sites) it has is at least $3.4 \times 10^9$ sites/mm$^2$, preferably at least $3.8 \times 10^9$ sites/mm$^2$, more preferably at least $4.2 \times 10^9$ sites/mm$^2$. Below $3.4 \times 10^9$ sites/mm$^2$, the cell sheet cannot develop adequate pumping function, thus failing to exhibit high functionality which is one of the characteristic features of the present invention.

As described above, the regenerated corneal endothelial cell sheet in the present invention is a highly populated cell sheet that can adhere very effectively to living tissues and which can function satisfactorily as a corneal endothelial tissue; it has not been possible at all to obtain such a cell sheet by the prior art.

The temperature responsive polymer which is used to cover the substrate of the cell culture support of the present invention will hydrate and dehydrate at varied temperatures, and it has been found that the effective temperature range is 0° C.-80° C., preferably 10° C.-50° C. more preferably 20° C.-45° C. Beyond 80° C., cells may die, which is not preferred. Below 0° C., the cell growth rate will generally drop by an extreme degree or cells will die, which also is not preferred.

The temperature responsive polymer to be used in the present invention may be a homopolymer or a copolymer. Examples of such polymers include the polymers described in JP 2-211865 A. Specifically, they are obtained by homo- or copolymerization of the following monomers. Monomers that can be used include, for example, (meth)acrylamide compounds ((meth)acrylamide refers to both acrylamide and methacrylamide, and this applies hereinafter), N- (or N,N-di)alkylsubstituted (meth)acrylamide derivatives, and vinyl ether derivatives: in the case of copolymers, any two or more of those monomers may be used. In addition, those monomers may be copolymerized with other monomers, or polymers may be grafted together or copolymerized, or alternatively, mixtures of polymers and copolymers may be employed. If desired, the polymers may be crosslinked to the extent that will not impair their properties.

The substrate that is to be covered with the temperature responsive polymer may be chosen from among the glass, modified glass, compounds such as polystyrene and poly (methyl methacrylate), and all other substances that can generally be given shape, as exemplified by polymer compounds other than those compounds, and ceramics.

The method of covering the support with the temperature responsive polymer is not limited in any particular way but one may follow the methods described in JP 2-211865 A. Specifically, the covering operation can be achieved by either subjecting the substrate and the above-mentioned monomers or polymers to electron beam (EB) exposure, γ-ray irradiation, ultraviolet irradiation, plasma treatment, corona treatment or organic polymerization reaction or by means of physical adsorption as effected by application of coating solutions or the kneading step.

The coverage of the temperature responsive polymer is suitably in the range of 0.4-3.0 μg/cm$^2$, preferably 0.7-2.8 μg/cm$^2$, more preferably 0.9-2.5 μg/cm$^2$. If the coverage of the temperature responsive polymer is less than 0.4 μg/cm$^2$, the cells on the polymer will not easily detach even if they are given a stimulus and the operating efficiency is considerably lowered, which is not preferred. If, on the other hand, the coverage of the temperature responsive polymer is greater than 3.0 μg/cm$^2$, cells will not easily adhere to the covered area and adequate adhesion of the cells becomes difficult to achieve.

The morphology of the support in the present invention is not limited in any particular way and may be exemplified by a dish, a multi-plate, a flask or a cell insert.

In the present invention, cell cultivation is effected on the cell culture support that has been prepared in the manner described above. The temperature of the culture medium is not limited in any particular way as long culture is effected at temperatures where the aforementioned polymer with which the substrate surface is covered dehydrates. It goes without saying that it is inappropriate to perform cultivation in a lower-temperature range where the cultured cells will not grow or in a higher-temperature range where the cultured cells will die. The culture conditions other than temperature may be as adopted in the usual method and are not limited in any particular way. For instance, the culture medium to be used may be one that is supplemented with serum such as known fetal calf serum (FCS); alternatively, it may be a serum-free medium. In the process of the present invention, the cultured cells may be detached and recovered from the support material by first bringing the cultured, regenerated corneal endothelial cell sheet into close contact with the carrier, then adjusting the temperature of the support material with adhering cells to the temperature at which the overlying polymer on the support substrate hydrates, whereupon the cells can be detached together with the carrier. In this case, smooth detachment can be realized by applying a water stream to the gap between the cell sheet and the support. Detachment of the cell sheet may be effected within the culture solution in which the cells have been cultivated or in other isotonic fluids, whichever is suitable depending on the object.

This is illustrated below with poly(N-isopropyl acrylamide) being taken as an exemplary temperature responsive polymer. Poly(N-isopropyl acrylamide) is known as a polymer having a lower critical dissolution temperature at 31° C. and if it is in a free state, it undergoes dehydration in water at temperatures above 31° C. and the polymer chains aggregate to cause turbidity. Conversely, at temperatures of 31° C. and below, the polymer chains hydrate to become dissolved in water. In the present invention, this polymer covers the surface of a substrate such as a Petri dish and is immobilized on it. Therefore, at temperatures above 31° C., the polymer on the substrate surface also dehydrates but since the polymer chains cover the substrate surface and are immobilized on it, the substrate surface becomes hydrophobic. Conversely, at temperatures of 31° C. and below, the polymer on the substrate surface hydrates but since the polymer chains cover the substrate surface and are immobilized on it, the substrate surface becomes hydrophilic. The hydrophobic surface is an appropriate surface for the adhesion and growth of cells whereas the hydrophilic surface is of such a nature as to defy the adhesion of cells and the cells being cultivated or the cell sheet will be detached simply by cooling.

The cell sheet of the present invention is populated with cells at high density. The process for producing the cell sheet is not limited in any particular way but considering the inability of corneal endothelial cells to grow rapidly to high density, an exemplary method that may be mentioned comprises performing several subcultures until a predetermined total cell count is reached, whereupon all cells that have grown are cultured over a predetermined area. In that instance, the concentration of cells in the cell dispersion may be increased by centrifugal concentrating or, alternatively, the area of cultivation on the substrate may be reduced to increase the cell count per unit area. The substrate to be used for subculture of cells is not limited in any particular way but cultivating corneal endothelial cells on adhesive proteins such as collagen IV, collagen I, collagen III, laminine, fibronectin and matrigel is advantageous since the cell morphology is kept intact.

The number of cells to be cultured per unit area of the substrate is suitably at least 2,000 cells/mm$^2$, preferably at least 2,300 cells/mm$^2$, and more preferably at least 2,500 cells/mm$^2$. Below 2,000 cells/mm$^2$, it becomes difficult to ensure that the regenerated corneal endothelial cell sheet obtained has a cell density of at least 2,500 cells/mm$^2$.

In the present invention, the cell sheet as pressed against the diseased part may be stripped of the carrier. The method of stripping the carrier is not limited in any particular way and may be exemplified by a method in which the carrier is wetted so that its adhesion to the cell sheet is made sufficiently weak to enable stripping of the carrier or by a method in which the carrier is cut off by a suitable means such as a scalpel, scissors, laser light or plasma waves. Take, for example, the case of using the cell sheet placed in close contact with the aforementioned carrier having a cutout in a selected area; if the cell sheet is cut along the boundary of the diseased part as by laser light, the cell sheet will not adhere to any unwanted area that is outside of the diseased part, which is advantageous for the purposes of the invention.

The method of fixing the regenerated corneal endothelial cell sheet shown in the present invention to a living tissue is not limited in any particular way; the cell sheet may be sutured to the living tissue; alternatively, since the regenerated corneal endothelial cell sheet shown in the present invention will rapidly take on the living tissue, the cell sheet, once adhered to the diseased part, need not be sutured to the living body.

In order to detach and recover the regenerated corneal endothelial cell sheet with high yield, the cell culture support may be lightly tapped or rocked, or the culture medium may be agitated with the aid of a pipette, or a water stream may be applied to the gap between the cell sheet and the substrate; these and other methods may be applied either independently or in combination. In addition, the cultured cells may optionally be washed with an isotonic fluid or the like so that they are detached for recovery.

The use of the regenerated corneal endothelial cell sheet shown in the present invention is not limited in any particular way but it may be effectively used against corneal endothelium disorders and bullous keratopathy.

The regenerated corneal endothelial cell sheet obtained by the process described above far excels what is obtained by the prior art methods in that it is non-invasive during detachment and features high capabilities, so it has a great potential in clinical applications, as exemplified by grafting corneal endothelial sheets. In particular, unlike the conventional graft sheets, the regenerated corneal endothelial cell sheet of the present invention has high take on living tissues and hence takes very rapidly on the living tissues. This contributes not only to improving the efficiency of treatment of a diseased part but also to reducing the burden on the patient, hence, it is anticipated to materialize as a very effective technique. Note that the cell culture support used in the process of the present invention allows for repeated use.

EXAMPLES

On the following pages, the present invention is described in greater detail by reference to examples which are by no means intended to limit the scope of the invention.

Examples 1 and 2

To a commercial 3.5 cm$^\Phi$ cell culture dish (FALCON 3001 manufactured by Becton Dickinson Labware), a coating solution having N-isopropylacrylamide monomer dissolved in isopropyl alcohol to give a concentration of 40 wt % (Example 1) or 45 wt % (Example 2) was applied in a volume of 0.1 ml. By applying electron beams with an intensity of 0.25 MGy, an N-isopropylacrylamide polymer (PIPAAm) was immobilized on the surface of the culture dish. After the irradiation, the culture dish was washed with ion-exchanged water to remove the residual monomer and the PIPAAm that did not bind to the culture dish; the culture dish was then dried in a clean bench and sterilized with an ethylene oxide gas to provide a cell culture support material. The coverage of PIPAAm was found to be 1.6 µg/cm$^2$ (Example 1) or 1.8 µg/cm$^2$ (Example 2).

In a separate step, a corneal endothelial tissue was collected from the corneal limbus of a white rabbit under deep anesthesia by the usual method and the collected corneal endothelial cells were passed through five subcultures in a collagen IV coated flask by the usual method (medium used: DMEM, 10% FCS, 37° C. under 5% $CO_2$). As the result, $4 \times 10^6$ corneal endothelial cells could eventually be recovered.

In the next step, all recovered cells were cultured on the cell culture support materials having PIPAAm immobilized on the surface of the above-described culture dish and they were kept cultivated for four consecutive weeks. After the cultivation, a carrier molded from a 2.3 cm$^\Phi$ polyvinylidene difluoride (PVDF) membrane having a 1.8 cm$^\Phi$ circular cutout in the center was placed over the cultured cells; the culture medium was gently aspirated through the cutout and was subjected to incubating and cooling at 20° C. for 30 minutes together with the cell culture support material, whereupon the cells on each of the cell culture support materials were detached together with the overlying carrier. Each of the cell sheets obtained had adequate strength as a single sheet, with a shrinkage of no more than 5%. The density of cells in each of the cell sheets obtained was 3,000 cells/mm$^2$.

In each of Examples 1 and 2, "low-temperature treatment" was performed by incubating at 20° C. for 30 minutes but the "low-temperature treatment" to be performed in the present invention is not limited to the above-indicated temperature and time. The preferred temperature condition for the "low-temperature treatment" which is to be performed in the present invention is in the range of 0° C.-30° C. and the preferred treatment time is in the range from two minutes to an hour.

The regenerated corneal endothelial cell sheets obtained in Examples 1 and 2 were transplanted in a white rabbit deficient of a corneal endothelial tissue portion. For grafting, the side of each regenerated corneal endothelial cell sheet opposite the side where it was in contact with the support was aspirated and secured to a fixture having a suction surface with the same curvature as the corneal endothelial tissue in a living body and the carrier was excised with a scalpel. With the aid of the fixture, each regenerated corneal endothelial cell sheet was pressed onto the wounded site and after stopping the sucking action of the fixture, the sheet was kept adhered for 15 minutes. After the excision, the regenerated corneal endothelial cell sheets were not sutured to the living tissue. Finally, the excised corneal tissue was sutured to the eyeball. Three weeks later, the diseased part was observed and the regenerated corneal endothelial cell sheets of Examples 1 and 2 were both found to have taken well on the eyeball, with no swelling of the cornea.

Example 3

A cell culture support material was prepared as in Example 1. Subsequently, a coating solution having an acrylamide monomer containing N,N-methylene bisacrylamide (1 wt %/acrylamide monomer) dissolved in isopropyl alcohol to give a concentration of 5 wt % was applied over the support material in a volume of 0.1 ml. A metallic mask having a diameter of 1.8 cm was superposed and while being kept in that state, the support material was exposed to electron beams with an intensity of 0.25 MGy, whereupon an acrylamide polymer (PAAm) was immobilized except in the area under the metallic mask. After the irradiation, the culture dish was washed with ion-exchanged water to remove the residual monomer and the PAAm that did not bind to the culture dish; the culture dish was then dried in a clean bench and sterilized with an ethylene oxide gas to provide a cell culture support material.

In the next step, by repeating the same procedure as Example 1, a corneal endothelial tissue was collected from the corneal limbus of a white rabbit under deep anesthesia and the collected corneal endothelial cells were passed through four subcultures, whereupon $7.6 \times 10^5$ corneal endothelial cells could eventually be recovered. In the next step, all recovered cells were cultured on the cell culture support material described above and they were kept cultivated for three consecutive weeks. As in Example 1, after the cultivation, a carrier molded from a 2.3 cm$^\Phi$ polyvinylidene difluoride (PVDF) membrane having a 1.8 cm$^\Phi$ circular cutout in the center was placed over the cultured cells; the culture medium was gently aspirated through the cutout and was subjected to incubating and cooling at 20° C. for 30 minutes together with the cell culture support material, whereupon the cells on the cell culture support material were detached together with the overlying carrier. The cell sheet obtained had adequate strength as a single sheet, with a shrinkage of no more than 5%. The density of cells in the cell sheet obtained was 2,800 cells/mm$^2$.

As in Example 1, the regenerated corneal endothelial cell sheet obtained was transplanted in a white rabbit deficient of a corneal endothelial tissue portion. Three weeks later, the diseased part was observed and the regenerated corneal endothelial cell sheet was found to have taken well on the eyeball, with no swelling of the cornea.

Comparative Example 1

A corneal endothelial cell sheet was prepared as in Example 2, except that the cell sheet was detached without using the carrier, whereupon it shrank by 42%.

As in Example 2, the corneal endothelial cell sheet obtained was transplanted in a rabbit that was deficient of a corneal endothelial tissue portion. At day 1 of the grafting, the diseased part was observed; the take of the corneal endothelial cell sheet on the eyeball was rather poor, with some swelling of the cornea.

Comparative Example 2

An attempt was made to prepare a regenerated corneal endothelial cell sheet as in Example 3, except that corneal endothelial cells were cultivated and the cell sheet was detached from the cell culture support 9 days after confluence was reached. As in Example 3, an attempt was made to detach the regenerated corneal endothelial cell sheet but it could be detached only partially and hence it was unsatisfactory as a cell sheet.

Example 4

As in Example 3, a cell culture support material was prepared using an overlying metallic mask with a diameter of 1.8 cm; then, corneal endothelial cells were collected from the human corneal limbus by repeating the procedure of Example 3 and cultured on the prepared cell culture support material; the cultured cells were kept cultured for four consecutive weeks. After the cultivation, using a polyvinylidene difluoride (PVDF) carrier, the cells were subjected to incubating and cooling at 20° C. for 30 minutes together with the cell culture support material, whereupon the endothelial cell sheet on the cell culture support material was detached. The endothelial cell sheet obtained had adequate strength as a single sheet, with a shrinkage of no more than 5%. The cell density in the obtained endothelial cell sheet was 3,000 cells/mm$^2$. The endothelial cell sheet thus obtained was stripped of the carrier to give the photographic image shown in FIG. 1, from which one can see that the human regenerated corneal endothelial cell sheet was suspended in the culture support material.

The human regenerated corneal cell sheet being cultivated were recovered at day 1 (FIG. 2A), day 3 (FIG. 2B), day 7 (FIG. 2C) and day 14 (FIG. 2D), and the produced collagen IV (upper row) and fibronectin (lower row) were stained in accordance with the usual method; the results are shown in FIGS. 2A-2D. Obviously, collagen IV and fibronectin were accumulated as the cultivation was performed for an increased number of days.

At day 4 of culture, ZO-1 protein in the regenerated corneal endothelial cell sheet was subjected to immunofluorescent staining and the result is shown in FIG. 3. Obviously, the protein was localized between cells, indicating that the regenerated corneal endothelial cell sheet obtained in the present invention had intercellular bonds which survived the cell detachment and remained intact.

Subsequently, the human regenerated corneal endothelial cell sheet was detached from within the culture support material. The collagen IV (left photo) and fibronectin (right photo) present in the human regenerated corneal cell sheet which was being detached were stained in accordance with the usual method and the results are shown in FIG. 4. As one can see from this figure, the regenerated corneal endothelial cell sheet obtained in Example 4 had both collagen IV and fibronectin.

FIG. 5 shows the results of H/E staining of the human regenerated corneal cell sheet as detached in Example 4 (left photo), as well as the results of staining, in accordance with the usual method, of the collagen IV (center photo) and fibronectin (right photo) present in the detached cell sheet. From the photo of H/E staining, one can see the following: the human regenerated corneal endothelial cell sheet obtained in the present invention is single-layered as corneal endothelial cells normally are in the living body; collagen IV is localized on the side of the endothelial cell sheet which was in contact with the support; fibronectin is localized between cells.

Another regenerated corneal cell sheet was prepared in a similar way, fixed with 2% glutaraldehyde, then osmate stained, and examined under a transmission electron microscope; the result is shown in FIG. 6. Obviously, the regenerated corneal cell sheet obtained had the same assembly as tissues in the living body.

Example 5

Figure 7B:
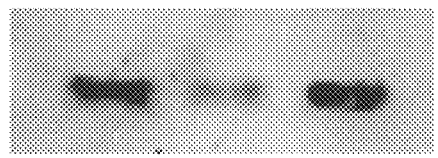

As in Example 1, a cell culture support material was prepared; then, corneal endothelial cells were collected from the human corneal limbus by repeating the procedure of Example 3 and cultured on the prepared cell culture support material; the cultured cells were kept cultured for four consecutive weeks. After the cultivation, the cells were subjected to incubating and cooling at 20° C. for 30 minutes together with the cell culture support material but without using a polyvinylidene difluoride (PVDF) carrier, whereupon the endothelial cell sheet on the cell culture support material was detached. The protein present in the surface layer of the endothelial cell sheet obtained and ZO-1 protein participating in intercellular binding were extracted in accordance with the usual method and verified by SDS-PAGE. The results are shown by T in FIGS. 7A-7B. FIG. 7A shows the results of staining with Coomassie Brilliant Blue to measure the protein present in the surface layer of the cell sheet, and FIG. 7B shows the results of staining with an anti-human ZO-1 polyclonal antibody. From FIGS. 7A-7B, one can see that in accordance with the method of the present invention, the protein in the cell surface layer was not broken but remained intact.

Comparative Examples 3 and 4

An experiment was conducted by repeating the procedure of Example 5 to perform culturing for 4 weeks, except that human corneal endothelial cells were cultivated on a commercial culture substrate which was not covered with a temperature responsive polymer. After the cultivation, the cultured cells were detached by two methods, one being dispase treatment as the usual method (Comparative Example 3) and the other being physical detachment with a rubber scraper (Comparative Example 4). The cells obtained by the respective methods were treated as in Example 5; the protein present in the surface layer of the endothelial cell sheets and ZO-1 protein participating in intercellular binding were extracted in accordance with the usual method and verified by SDS-PAGE. The results are shown by D in FIG. 7 (Comparative Example 3) and by S in FIG. 7 (Comparative Example 4). From FIG. 7, one can see that in the dispase treatment, the protein in the cell surface layer was broken and remained intact in a decreased amount. In the scraper method, a large amount of protein remained intact in the cell surface layer; however, due to the physical detachment, the corneal endothelial cell sheet obtained had so many cuts that it was unsatisfactory as the regenerated corneal endothelial cell sheet shown in the present invention. Comparing S and T in FIG. 7, one can recognize no difference at all, which indicates that the protein in the surface layer of the regenerated corneal endothelial cell sheet obtained in Example 5 was hardly broken.

Example 6

Using the yet-to-be-detached, regenerated corneal endothelial sheet obtained in Example 3, as well as a regenerated corneal endothelial sheet that was detached by cooling and again adhered to a commercial 3.5 cm$^\Phi$ cell culture dish (FALCON 3001), the number of pumps per cell was counted both before and after detachment.
Specifically, the total amount of uabaine binding was measured on the assumption that one molecule of uabaine as a Na—K ATPase inhibitor would bind to one molecule of Na—K pump. The uabaine had been labelled with $^3$H and measurements were done by a liquid scintillation counter. From the total amount of uabaine binding to the cell sheet and from the cell density of the cell sheet, the number of pumps per cell was counted both before and after detachment in Example 3: the pre-detachment value was $3.5 \times 10^6$ pumps and the post-detachment value was $3.5 \times 10^6$ pumps. The cell culture support of the present invention had the advantage that it could be detached without causing any damage to cells.

Example 7

Figure 8A:
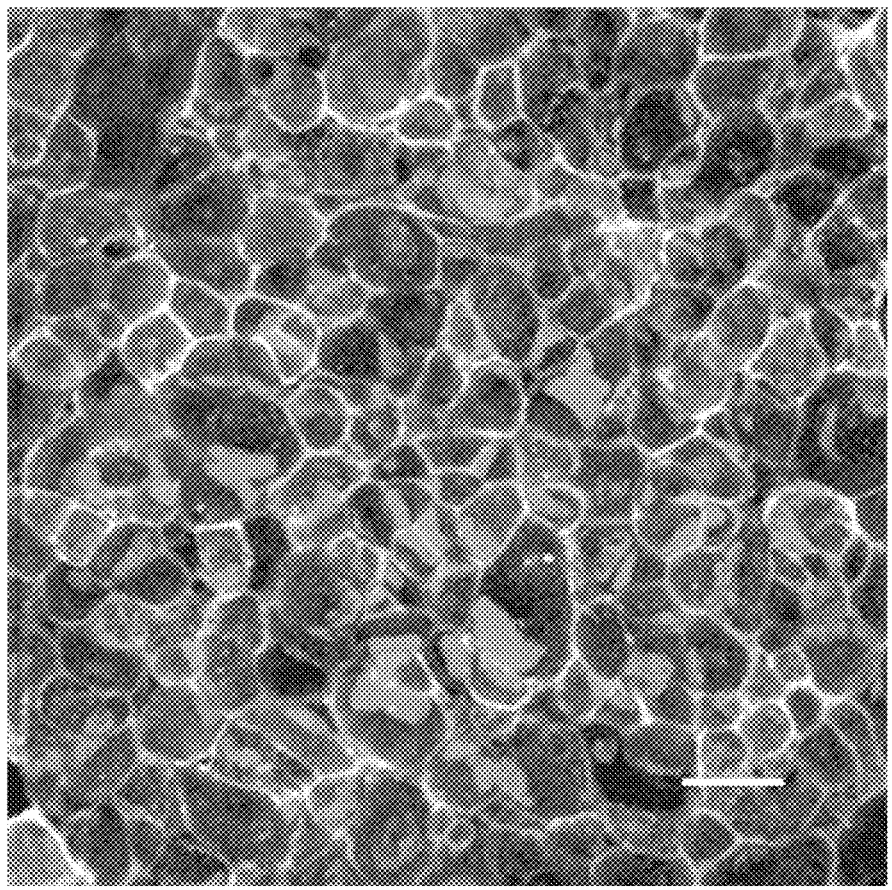
FIGS. 8A-8B show the results of an experiment in which the yet-to-be-detached, regenerated corneal endothelial sheet obtained in Example 7 was stained with an anti-rabbit Na—K ATPase monoclonal antibody so that the Na—K ATPase pump sites were stained green whereas the cell nuclei were stained red with propidium iodide, followed by examination with a confocal microscope.
Figure 8B:

As in Example 3, a cell culture support material was prepared using an overlying metallic mask with a diameter of 1.8 cm; then, corneal endothelial cells were collected from the human corneal limbus by repeating the procedure of Example 3 and cultured on the prepared cell culture support material; the cultured cells were kept cultured for four consecutive weeks. The yet-to-be-detached, human regenerated corneal endothelial sheet was stained with an anti-rabbit Na—K ATPase monoclonal antibody so that the Na—K ATPase pump sites were stained green; at the same time, the cell nuclei were stained red with propidium iodide. The results of examination with a confocal microscope are shown in FIG. 8; the upper plate A shows the result of observing the cultured cell sheet from above, and B shows the result of observation in the thickness direction. Obviously, the regenerated corneal endothelial cell sheet of the present invention retained Na—K ATPase pump sites at high density.

Example 8

Figure 9A:
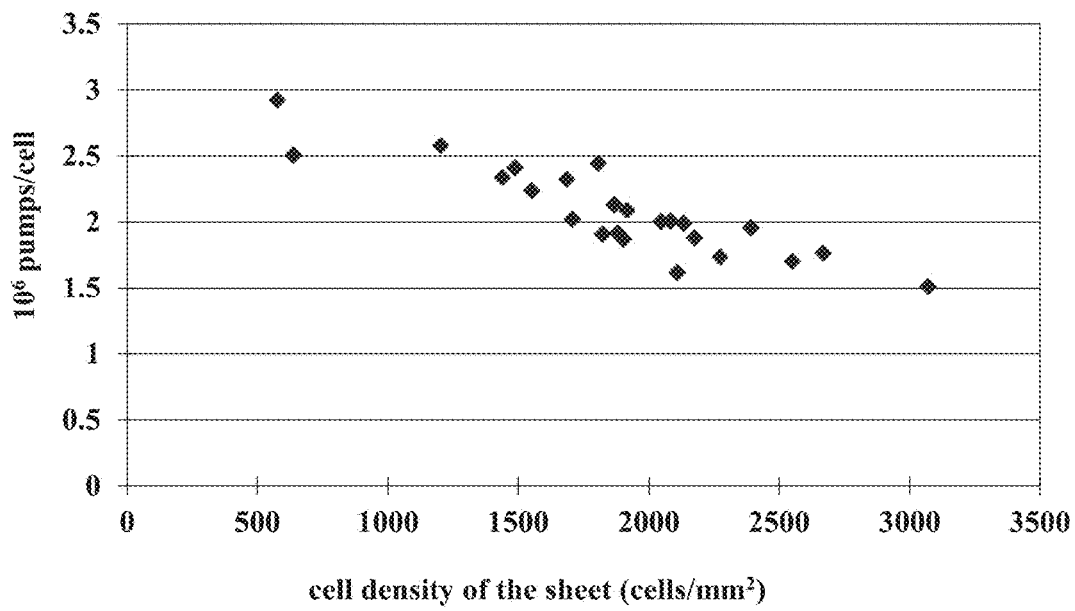
FIG. 9A shows the correlation of the number of pumps per cell vs. the density of cells in the human corneal endothelial cell sheet.
Figure 9B:
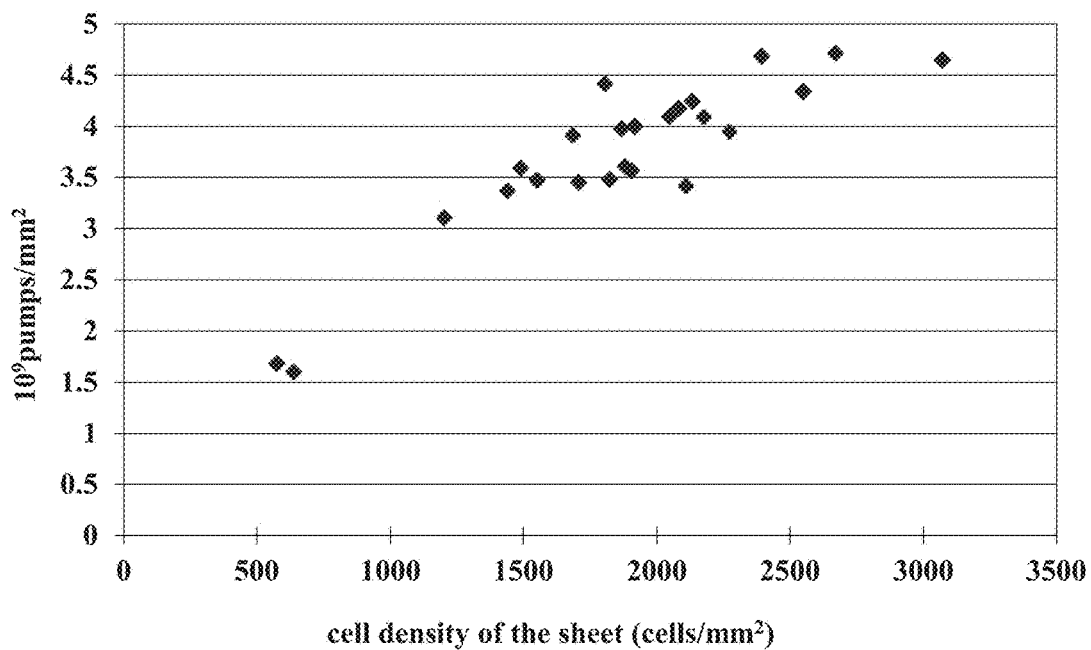
FIG. 9B shows the correlation of the number of pumps per unit area vs. cell density.

The cultivation procedure of Example 6 was repeated, except that human corneal endothelial cells were cultured until the cell density in the cell sheet was in the range from 575 cells/mm$^2$ to 3,070 cells/mm$^2$. As in Example 6, the number of Na—K ATPase pump sites was counted by measuring the amount of $^3$H labelled uabaine binding with a liquid scintillation counter. From the number of Na—K ATPase pump sites and from the cell density of the cell sheet, the number of pumps per cell in the detached, regenerated corneal endothelial cell sheet was counted. The results are shown in FIG. 9A, the correlation of the number of pumps per cell vs. cell density; FIG. 9B, the correlation of the number pumps per unit area vs. cell density. From FIG. 9A, it can be seen that the number of pumps per cell decreases with increasing cell density: from FIG. 9B, it can be seen that the number of pumps per unit area increases with increasing cell density. It became clear that the number of pump sites desired in the present invention could be reached when the cell density was increased to 2,500 cells/mm$^2$.

Comparative Example 5

A commercial 3.5 cm$^\Phi$ cell culture dish (FALCON 3001) was overlaid as in Example 3 with 0.1 ml of a coating solution having an acrylamide monomer containing N,N-methylene bisacrylamide (1 wt %/acrylamide monomer) dissolved in isopropyl alcohol to give a concentration of 5 wt %. A metallic mask having a diameter of 1.8 cm was superposed and while being kept in that state, the culture dish was exposed to electron beams with an intensity of 0.25 MGy, whereupon an acrylamide polymer (PAAm) was immobilized except in the area under the metallic mask. After the irradiation, the culture dish was washed with ion-exchanged water to remove the residual monomer and the PAAM that did not bind to the culture dish; the culture dish was then dried in a clean bench and sterilized with an ethylene oxide gas to provide a culture support which was the same as the cell culture support of Example 3 except that it had no PIPAAm-coverage area.
Using this culture support together with the yet-to-be-detached, regenerated corneal endothelial sheet obtained in Example 4, as well as a regenerated corneal endothelial sheet that was detached by collagenase treatment and again adhered to a commercial 3.5 cm$^\Phi$ cell culture dish (FALCON 3001), the number of pumps per cell was counted both before and after detachment. The pre-detachment value was $3.5 \times 10^6$ pumps and the post-detachment value was $1.5 \times 10^6$ pumps. The damage to cells upon detachment was significant.

INDUSTRIAL APPLICABILITY

The regenerated corneal endothelial cell sheets obtained by the present invention feature very high take on living tissues and exhibit high capabilities, so they have a great potential for use in clinical applications including treatment of corneal endothelial diseases. Hence, the present invention will prove very useful in medical and biological fields such as cell engineering and medical engineering.

The invention claimed is:

1. A cultured corneal endothelial cell sheet in close contact with a carrier, wherein the cell sheet cultivated on a cell culture support has been detached together with the carrier from the cell culture support after bringing the cell sheet into close contact with the carrier, without any treatment with a proteolytic enzyme, wherein the cell sheet has a cell density of at least 2,500 cells/mm$^2$ and at least $3.4 \times 10^9$ pump sites/mm$^2$; wherein the carrier is a circular carrier with a cutout in the center and is removable from the cell sheet.

2. The cultured corneal endothelial cell sheet according to claim 1, wherein the cell sheet has shrinkage not greater than 20% after detachment from the cell culture support.

3. The cultured corneal endothelial cell sheet according to claim 1, wherein the cell sheet has at least 80% of a basement membrane protein left intact.

4. The cultured corneal endothelial cell sheet according to claim 1, wherein the cell sheet has at least 80% of a desmosome structure left intact.

5. The cultured corneal endothelial cell sheet according to claim 1 for treating a diseased part of a cornea, wherein the diseased part of the cornea is partly or entirely damaged or defective.

6. The cultured corneal endothelial cell sheet according to claim 1, wherein the cell sheet is capable of being applied to a diseased or damaged part of a cornea such that the diseased or damaged part is covered without suturing.

7. The cultured corneal endothelial cell sheet according to claim 1, which is cut to the size and shape of a diseased or damaged part of a cornea before being applied to cover the diseased or damaged part.

8. A process for producing a cultured corneal endothelial cell sheet in close contact with a carrier, comprising:
   (a) culturing corneal endothelial cells on a cell culture support to generate a corneal endothelial cell sheet, wherein the surface of the cell culture support is covered with a polymer having a hydrating force varying in a temperature range of 0-80° C.;
   (b) after said culturing, adjusting the temperature of the culture to a temperature at which the polymer is hydrated;
   (c) bringing the carrier into close contact with the corneal endothelial cell sheet, wherein the carrier is a circular carrier with a cutout in the center and is removable from the cell sheet; and
   (d) detaching the cell sheet together with the carrier from the cell culture support, without any treatment with a proteolytic enzyme, wherein the cell sheet has a cell density of at least 2,500 cells/mm$^2$ and at least $3.4 \times 10^9$ pump sites/mm$^2$.

9. The process according to claim 8 further comprising culturing the corneal endothelial cells through multiple subcultures prior to the culturing step of (a).

10. The process according to claim 9, wherein the subcultures are performed on collagen IV.

11. The process according to claim 8, wherein the polymer is poly(N-isopropylacrylamide).

12. The process according to claim 8, wherein the cell sheet shrinkage is not greater than 20% after detachment from the cell culture support.

13. A method of treating a patient having corneal endothelial tissue that is partly or entirely damaged or defective, comprising: grafting the cultured corneal endothelial cell sheet of claim 1 onto the corneal endothelial tissue where it is partly or entirely damaged or defective.

14. A method of using a cultured corneal endothelial cell sheet produced by the process according to claim 8 for treating a patient having corneal endothelial tissue that is partly or entirely damaged or defective, comprising:
   (e) securing the cell sheet to a fixture on the side of the cell sheet that is opposite where it was in contact with the cell culture support, wherein the fixture has the same curvature as the morphology of the corneal endothelial tissue in a living body;
   (f) covering the damaged or defective corneal endothelial tissue in a manner that allows for removal of the fixture and the carrier; and
   (g) removing the fixture and the carrier from the cell sheet.

15. A method of using a cultured corneal endothelial cell sheet produced by the process according to claim 8 for treating a patient having corneal endothelial tissue that is partly or entirely damaged or defective, comprising:
   (e) securing the cell sheet to a fixture on the side of the cell sheet that is opposite where it was in contact with the cell culture support, wherein the fixture has the same curvature as the morphology of the corneal endothelial tissue in a living body;
   (f) removing the carrier from the cell sheet;
   (g) covering the damaged or defective corneal endothelial tissue in a manner that allows for removal of the fixture; and
   (h) removing the fixture from the cell sheet.

16. The method according to claim 13, wherein the grafted cell sheet covers the damaged or defective corneal endothelial tissue without suturing.

17. The method according to claim 13 further comprising cutting the cell sheet to a size and shape that covers the damaged or defective corneal endothelial cell tissue before grafting the cell sheet.

18. The method according to claim 13, wherein the treated patient has corneal endothelial disorder or bullous keratopathy.

19. The process according to claim 8, wherein the cell sheet is detached not earlier than 10 days after cells have become confluent on the cell culture support.

20. The cultured corneal endothelial cell sheet according to claim 1, which is detached not earlier than 10 days after cells have become confluent on the cell culture support.

* * * * *